(12) United States Patent
Schoen et al.

(10) Patent No.: US 6,602,880 B2
(45) Date of Patent: Aug. 5, 2003

(54) 3-PHENYL-3,7-DIAZABICYCLO[3.3.1] NONANE COMPOUNDS, PROCESS FOR PREPARING THEM, PHARMACEUTICAL COMPOSITIONS CONTAINING THEM AND USE THEREOF TO INHIBIT CARDIAC ARRHYTHMIA

(75) Inventors: Uwe Schoen, Burgdorf (DE); Josef Messinger, Sehnde (DE); Reinhard Brueckner, Hannover (DE); Dieter Ziegler, Hemmingen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 46 days.

(21) Appl. No.: 10/183,038

(22) Filed: Jun. 27, 2002

(65) Prior Publication Data

US 2003/0109541 A1 Jun. 12, 2003

(30) Foreign Application Priority Data

Jun. 28, 2001 (DE) .......................... 101 31 217

(51) Int. Cl.$^7$ ...................... A61K 31/44; C07D 471/08; C07D 471/10
(52) U.S. Cl. ...................... 514/278; 514/300; 546/18; 546/122
(58) Field of Search .................... 546/122, 18; 514/278, 514/300

(56) References Cited

U.S. PATENT DOCUMENTS

| | | | |
|---|---|---|---|
| 4,550,112 A | 10/1985 | Schoen et al. | 514/278 |
| 4,912,113 A | 3/1990 | Schoen et al. | 514/278 |
| 5,532,251 A | 7/1996 | Schoen et al. | 514/300 |
| 5,576,327 A | 11/1996 | Schoen et al. | 514/300 |
| 5,635,511 A | 6/1997 | Schoen et al. | 514/278 |

FOREIGN PATENT DOCUMENTS

| | | |
|---|---|---|
| DE | 2658558 A1 | 12/1976 |
| EP | 103 833 B1 | 9/1983 |
| EP | 306 871 B1 | 9/1988 |
| EP | 665 014 B1 | 1/1995 |
| EP | 665 228 B1 | 1/1995 |

OTHER PUBLICATIONS

Hamill et al., "Improved Patch–Clamp Techniques for High– Resolution Current Recording from Cells and Cell-–Free Membrane Patches". *Pfluegers Arch* 391:85–100 (1981).

Zhou et al., "Properties of HERG Channels Stably Expressed in HEK 293 Cells Studied at Physiological Temperature". *Biophys. Journal* 74:230–241 (1998).

Hondeghem et al., "Instability and Triangulation of the Action Potential Predict Serious Proarrhythmia, but Action Potential Duration Prolongation is Antiarrhythmic". *Circulation* 2004–2013 (2001).

Hondeghem, "Computer Aided Development of Antiarrhythmic Agents with Class III$_a$ Properties". Journal of Cardiovascular Electrophysiology vol. 5, No. 8, 711–721 (1994).

Primary Examiner—Bernard Dentz
(74) Attorney, Agent, or Firm—Crowell & Moring LLP

(57) ABSTRACT

Pharmacologically active compounds of the general formula I

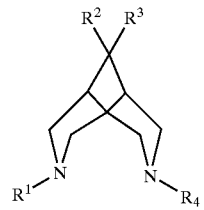

I wherein
  $R^1$ is an alkyl group with 1–6 carbon atoms or a cycloalkylalkyl group with 4–7 carbon atoms,
  $R^2$ is lower alkyl, and
  $R^3$ is lower alkyl, or
  $R^2$ and $R^3$ together form an alkylene chain with 3–6 carbon atoms, and
  $R^4$ represents a phenyl radical monosubstituted in the ortho or para position by nitro, cyano or lower alkanoyl or disubstituted in the ortho and para positions by nitro, and
their physiologically compatible acid addition salts are described.

8 Claims, No Drawings

3-PHENYL-3,7-DIAZABICYCLO[3.3.1] NONANE COMPOUNDS, PROCESS FOR PREPARING THEM, PHARMACEUTICAL COMPOSITIONS CONTAINING THEM AND USE THEREOF TO INHIBIT CARDIAC ARRHYTHMIA

BACKGROUND OF THE INVENTION

The present invention relates to novel 3,7,9,9-tetrasubstituted 3,7-diazabicyclo[3.3.1]nonane compounds which bear a substituted phenyl radical in position 3, and to their salts and to pharmaceutical preparations containing these compounds and to processes for the preparation of these compounds and to the use of these compounds for inhibiting cardiac arrhythmia in mammals.

3-Benzoyl-3,7-diazabicyclo[3.3.1]nonane derivatives with antiarrhythmic properties are already known from U.S. Pat. No. 5,532,251 (=EP 665,014).

Furthermore, 3-phenylsulfonyl-3,7-diazabicyclo [3.3.1]nonane derivatives and medicaments containing them with antiarrhythmic properties are known from U.S. Pat. No. 5,576,327 and 5,635,511 (=EP 665,228).

Despite the efforts of the art, however, there has remained a need for active substances with effective antiarrhythmic activity.

SUMMARY OF THE INVENTION

It is an object of the present invention to provide new antiarrhythmic active substances with an improved activity profile.

Furthermore, it is an object of the invention to provide new 3,7-diazabicyclo[3.3.1]nonane compounds having valuable pharmacological properties.

These and other objects are achieved in accordance with the present invention by providing a compound corresponding to the formula I:

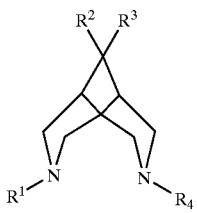

I wherein
  $R^1$ is an alkyl group with 1–6 carbon atoms or a cycloalkylalkyl group with 4–7 carbon atoms,
  $R^2$ is lower alkyl, and
  $R^3$ is lower alkyl, or
  $R^2$ and $R^3$ together form an alkylene chain with 3–6 carbon atoms, and
  $R^4$ represents a phenyl radical monosubstituted in the ortho or para position by nitro, cyano or lower alkanoyl or disubstituted in the ortho and para positions by nitro;
  or a physiologically compatible acid addition salt thereof.

It has now been found that the novel 3,7,9,9-tetrasubstituted 3,7-diazabicyclo[3.3.1]nonane compounds bearing a substituted phenyl radical in position 3 possess valuable pharmacological properties for the treatment and/or prophylaxis of cardiac arrhythmias and exhibit an antiarrhythmic action profile which makes them particularly suitable for the treatment of cardiac arrhythmias, in particular tachycardic arrhythmias.

The invention therefore relates to novel compounds of the general formula I

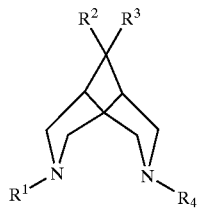

I wherein
  $R^1$ is an alkyl group with 1–6 carbon atoms or a cycloalkylalkyl group with 4–7 carbon atoms,
  $R^2$ is lower alkyl, and
  $R^3$ is lower alkyl, or
  $R^2$ and $R^3$ together form an alkylene chain with 3–6 carbon atoms, and
  $R^4$ represents a phenyl radical monosubstituted in the ortho or para position by nitro, cyano or lower alkanoyl or disubstituted in the ortho and para position by nitro,
  and their physiologically compatible acid addition salts.

If $R^1$ in the compounds of Formula I represents an alkyl group, this may be straight-chain or branched and contain 1 to 6, preferably 3 to 5, in particular 4, carbon atoms. A cycloalkylalkyl group $R^1$ may preferably be cyclopropylmethyl. Alkyl radicals with 3 to 5 carbon atoms have proved particularly suitable radicals $R^1$.

If the substituents $R^2$ and $R^3$ represent lower alkyl, these alkyl groups may be straight-chain or branched and contain 1 to 4, preferably 1 to 3, carbon atoms and in particular represent methyl.

If $R^2$ and $R^3$ together form an alkylene group, this may contain 3 to 6, preferably 4 to 5, carbon atoms. In particular, those compounds in which $R^2$ and $R^3$ together represent an alkylene chain with 4 to 5 carbon atoms have proved suitable.

The substituent $R^4$ represents a substituted phenyl group, in which the substituents of the phenyl group are arranged in the ortho or para position. A lower alkanoyl substituent may contain 2 to 5, preferably 2 to 3, carbon atoms. Preferably $R^4$ represents a phenyl group substituted in the para position by cyano or lower alkanoyl, in particular cyano.

According to the invention, the novel compounds of Formula I and their acid addition salts are obtained by reacting compounds of the general formula II

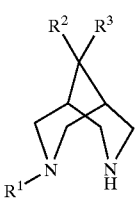

II wherein $R^1$, $R^2$ and $R^3$ have the above meanings, in known manner with compounds of the general formula III $R^4$—X    III wherein $R^4$ has the above meaning and X is halogen, and optionally free bases of Formula I are converted into their acid addition salts or the acid addition salts are converted into the free bases of Formula I.

The reaction of the compounds of Formula II with compounds of Formula III can take place in known manner under conventional conditions for the substitution of aromatic halides by amines. In particular chlorine or fluorine are considered as halogens in the compounds of Formula II. The reaction is carried out in an organic solvent which is inert under the reaction conditions, at temperatures between room temperature and the boiling temperature of the reaction mixture. Suitable organic solvents include, for example, ethers, in particular cyclic ethers such as tetrahydrofuran, lower alkanols such as butanol, lower aliphatic ketones such as acetone, dimethyl sulfoxide, dimethyl formamide, aromatic hydrocarbons such as benzene or toluene or mixtures of the above solvents. Advantageously, the reaction may be carried out under basic conditions e.g. in the presence of an at least equivalent amount of a base. Examples of suitable bases include inorganic bases such as alkali metal hydroxides, alkali metal carbonates, alkali metal amides or alkali metal hydrides and organic bases such as tertiary lower alkylamines.

The compounds of Formula I may be isolated from the reaction mixture and purified in a known manner. Acid addition salts can be converted into the free bases in conventional manner, and these may if desired be converted in known manner into pharmacologically compatible acid addition salts.

Suitable pharmacologically acceptable acid addition salts of the compounds of Formula I include, for example, the salts thereof with the usual inorganic acids, e.g. hydrohalic acids, in particular hydrochloric acid, sulfuric acid or phosphoric acids, or with organic acids, for example lower aliphatic mono-, di- or tricarboxylic acids such as maleic acid, fumaric acid, lactic acid, tartaric acid, acetic acid or citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid.

If the substituents $R^2$ and $R^3$ are different in the compounds of Formula I, the compounds contain an asymmetric center and may exist in two optically, active forms or as a racemate. The present invention includes both the racemic mixtures and the optical isomers of these compounds of Formula I. The optically active compounds can be obtained from the racemic mixtures in a known manner by customary separation processes, e.g. by chromatography on chiral separating materials or by fractional crystallisation of suitable salts using optically active acids. Enantiomerically pure compounds can also be prepared by synthesis from corresponding enantiomerically pure starting compounds of Formula II.

The starting compounds of Formula II are known from published German patent application no. DE 26 58 558, U.S. Pat. No. 4,450,112 (=EP 103,833), and U.S. Pat. No. 4,912, 113 (=EP 306,871) and/or can be prepared in a known manner by the methods described in these specifications or analogously to the methods described in these specifications.

The starting compounds of Formula III are known and/or can be prepared using known processes or analogously to known processes.

It has now surprisingly been found that the compounds of Formula I according to the invention and their physiologically acceptable acid addition salts have particularly beneficial antiarrhythmic effects. In particular, they exhibit class III antiarrhythmic properties, which cause a prolongation of the QT interval in the ECG and effect prolongation of the effective refractory period in the heart. The compounds have a beneficial activity profile with good compatibility, a long duration of action and such a high selectivity of the antiarrhythmic action with respect to hypotensive properties that in the antiarrhythmically effective dose range a therapeutically undesired effect on the blood pressure does not occur. The compounds are distinguished in that the antiarrhythmic action is particularly highly pronounced under tachycardic conditions. Furthermore, the compounds according to the invention have properties which make it possible to conclude that their antiarrhythmic properties are accompanied by surprisingly slight proarrhythmogenic side-effects.

The antiarrhythmic activity of the compounds can be demonstrated by standard pharmacological test methods. The example numbers given in the test methods for the individual test substances each relate to the preparation examples which follow.

Description of the Pharmacological Test Methods
1. Determination of the Minimum Toxic Dose Male mice each having a weight of 20 to 25 g were administered maximum doses of 300 mg/kg of the test substance p.o. The animals were observed carefully for toxicity symptoms for 3 hours. Additionally all symptoms and deaths were recorded over a period of 72 hours after administration. Concomitant symptoms were likewise observed and recorded. If death or severe toxic symptoms were observed, further mice were administered increasingly lower doses until toxic symptoms no longer occurred. The lowest dose which caused death or severe toxic symptoms is indicated in the following Table A as the minimum toxic dose.

TABLE A

| Test substance Example No. | Minimum toxic dose mg/kg mouse p.o. |
| --- | --- |
| 1 | 300 |
| 2 | 300 |

2. In vivo Investigation of the Antiarrhythmic Properties of the Substances under Tachycardic Conditions in Anaesthetised Guinea Pigs.

The effects of the substances on the effective refractory period (=ERP) and the blood pressure on i.v. administration with increased heart rate were investigated on anaesthetised guinea pigs. A bipolar stimulation catheter was inserted into the right ventricle of the animals via a jugular vein under full anaesthesia. The heart rates of the animals were kept at about 150% of their normal heart rates via this catheter by means of electrical stimulation during the entire investigation. A cannula for i.v. administration of the test substances was inserted in the other jugular vein. During the investigation, the systolic and the diastolic arterial blood pressure (=SAP and DAP) were measured in a carotid artery via a pressure gauge (Statham pressure transducer). The test substances were administered i.v. in increasing doses (cumulatively). Before administration of the first dose and in each case 8 minutes after administration of each dose, the ERP was determined by means of a double pulse protocol. The dose at which a prolongation of the ERP to 115% of the starting value was achieved was considered as the effective dose (=ERP-$ED_{115}$). Effective doses for a hypotensive effect were considered as the dose at which the SAP was decreased to 85% of its starting value (=SAP-$ED_{85}$), and the dose at which the DAP was decreased to 85% of its starting value (=DAP-$ED_{85}$).

The results obtained using the method described above are given in the following Table B.

TABLE B

| Example No. | Antiarrhythmic action ERP-ED$_{115}$ in μmol/kg i.v. | Vasodepression* ED$_{85}$ in μmol/kg i.v. | |
| --- | --- | --- | --- |
| | | DAP | SAP |
| 1 | 0.4 | >>10 | >>10 |
| 2 | 1 | 5 | 5 |

*>> indicates that at the doses tested no tendency to vasodepression could be detected.

3. In vitro Determination of the Action of the Test Substances on the Functional Refractory Period on Electrically Stimulated Papillary Muscles from Guinea-pig Hearts.

The action of the substances prolonging the refractory period can also be demonstrated in vitro tests by determination of the functional refractory period (=FRP) on the isolated papillary muscle of the right ventricle of guinea pigs.

The heart was quickly removed from guinea pigs which had been sacrificed by a blow to the back of the neck and the papillary muscles of the right ventricle were fixed in organ baths through which temperature-controlled oxygenated nutrient solution flowed. The muscle preparations were electrically stimulated with a frequency of 3 Hz. The test substances were added to the organ baths in increasing concentrations (cumulatively). In each case 20 minutes after addition of the test substance, the functional refractory period was determined by means of a double pulse protocol. In each case a cumulative concentration/action curve was plotted from the measured values. The concentration at which a prolongation of the FRP by 12 milliseconds was achieved was calculated from this as the effective concentration (=FRP-EC$_{+12ms}$).

The results obtained using the method described above are given in the following Table C.

TABLE C

| Example No. | Antiarrhythmic action FRP-EC$_{+12\ ms}$ in μmol/l |
| --- | --- |
| 1 | 0.6 |
| 2 | 0.7 |
| 3 | 0.6 |
| 4 | 0.8 |

4. In vitro Determination of the Potential Proarrhythmogenity of the Substances on Isolated Perfused Rabbit Hearts The extent of the potential proarrhythmogenity of Class III antiarrhythmic substances can be estimated using the measurement of electrophysiological parameters such as "instability" and "triangulation" (see below) on the monophasic action potential, derived from isolated perfused rabbit hearts. The pharmacological test set forth below was performed analogously to the method fundamentally described in L. M. Hondeghem et al., Circulation 103 (2001) 2004–2013 (referred to hereafter as "Hondeghem et al."), in conjunction with L. M. Hondeghem, Journal of Cardiovascular Electrophysiology 5(8) (1994) 711–721 (referred to hereafter as "Hondeghem"). The hearts were quickly removed from rabbits which had been sacrificed by a blow to the back of the neck, and were immediately perfused in a Langendorff arrangement under constant pressure (80 cm $H_2O$) with temperature-controlled oxygenated nutrient solution. The heart was stimulated with different stimulation protocols using two stimulation electrodes which were each arranged in the region of the right and left crus of the bundle of His (cf. "Hondeghem et al."). Two further electrodes (one discharge electrode endocardially in the region of the septum of the left ventricle and a reference electrode epicardially on the left ventricle) served to discharge the monophasic action potential.

Using the monophasic action potential duration with different repolarisation levels (APD10–90; "APD10" designates the action potential duration until the occurrence of 10% of repolarisation), the following parameters were derived as indicators of the proarrhythmogenity:

(1) Instability: The change in the APD60 from heartbeat to heartbeat is designated "instability". Under control conditions, this value is on average about 7 milliseconds (=ms). Greater deviations from this average value towards a longer duration (>7 ms) indicate an increased probability of occurrence for proarrhythmias caused by the test substances investigated.

(2) Triangulation: The repolarisation time in ms from APD30 to ADP90 is designated "triangulation". Under control conditions, this value is usually about 90 ms. A repolarisation time which is prolonged significantly beyond this control value under the influence of a test substance indicates a slower repolarisation process, which in turn may lead to an increased rate of subsequent polarisations (=proarrhythmias).

The results obtained with the method described above on three hearts (n=3) in each case are reproduced in the following Table D.

TABLE D

| Example No. | Concentration | Instability [ms] | Triangulation [ms] |
| --- | --- | --- | --- |
| 4 | 0.3 μM | 6/3/3 | 48/64/62 |
| | 1 μM | 6/25/7 | 52/79/79 |

5. Blocking Action on the Rapid or Slow Delayed Rectifier Potassium Current, "iKr" or "iKs", Respectively The principle of action of what are called class III antiarrhythmic substances (according to Vaughan-Williams) is based on their blocking of various cellular outward potassium currents which participate in repolarisation of the cardiac action potential. This leads to a prolongation of the cardiac refractory period, by means of which cardiac arrhythmias can be prevented. In this case, the proarrhythmogenic risk of class III antiarrhythmic substances depends on which potassium current or which combination of potassium currents is blocked. It is known from the literature that selective iKr-blocking may hold a high proarrhythmogenic risk, whereas the simultaneous blocking of the iKr and iKs is ascribed a clearly reduced proarrhythmogenic risk.

The iKs can be measured selectively in the manner described below: the hearts are quickly removed from anaesthetised dogs and a muscle section from the left ventricle is perfused with collagenase-containing solution via an arterial vessel. The well-dissociated tissue is comminuted and the individualised cardiac muscle cells are investigated electrophysiologically using the "whole-cell patch-clamp" method (cf. O. P. Hamill et al., Pflütgers Archive 391(2) (1981) 85–100): for selective investigation of the blocking action on the iKs, the inward calcium current is blocked by addition of 1 μM nisoldipine (=selective blocker of the inward calcium current), the iKr by addition of 2μM E-4031 (=selective iKr blocker) and the rapid inward sodium current and the transient outward potassium current by a holding potential of −40 mV. The iKs is then determined using the current amplitude immediately after a 5-second pulse protocol of −40 mV holding potential at most +50 mV depolarisation.

The iKr (HERG) can be measured selectively in the manner stated below: to measure the iKr, a cell line (human embryonal kidney cells, HEK293; see e.g. American Tissue Culture Collection (=ATCC) No.: CRL-1573) is used, which is stably transfected with the gene for the iKr (HERG) (cf. Z. Zhou et al., Biophysical Journal 74(1) (1998) 230–241). Since the cells used do not have any further ion currents which would disrupt the measurement, it is possible to dispense with the corresponding additions of channel-blocking substances. The iKr is determined using the current amplitude at −40 mV holding potential immediately after a 500 ms pulse protocol of −75 mV holding potential at most +10 mV depolarisation. That substance concentration at which 50% of the maximum current is blocked (IC50 %) is determined from the inhibitions of the corresponding current at different substance concentrations. The results obtained with the methods described above are reproduced in Table E below:

TABLE E

| Example No. | IC50 % - iKs | IC50 % - iKr |
|---|---|---|
| 3 | 0.7 $\mu$M | 0.09 $\mu$M |
| 4 | 0.7 $\mu$M | 0.02 $\mu$M |

In a further in vivo test on anaesthetised cats, the compound of Example 4 after administration p.o. and i.v. in each case exhibited a dosage-dependent, clear, long-lasting increase in the fibrillation threshold, which was more marked on the atrium than on the ventricle. Such an atrioselective increase in the fibrillation threshold is an indication that the tested compound has a beneficial action profile with a reduced proarrhythmogenity risk.

The foregoing test results show that the compounds of Formula I possess antiarrhythmic effects and clearly prolong the effective refractory period of the cardiac muscle, and that an effective hypotensive action of the substances occurs only at doses which are considerably higher than the doses which are effective for prolonging the refractory period. The above test results also indicate a connection between the surprisingly low tendency of the substances according to the invention to develop proarrhythmogenic side-effects and their specific profile of the influencing of the different outward-directed potassium currents in heart cells of larger mammals and humans, for example the influencing of the iKr and iKs.

Due to their activity profile described above, the substances are suitable for the suppression or inhibition of tachycardic cardiac arrhythmias and can be used for the prophylaxis and treatment of cardiac arrhythmias in larger mammals and humans. In particular, the substances are suitable for preventing the occurrence of tachyarrhythmias, i.e. arrhythmias which are coupled to an increase in the heart rate.

The doses to be used may vary individually and will naturally vary according to the type of condition to be treated, the substance used and the form of administration. In general, however, medicinal forms with an active substance content of 0.5 to 100 mg per individual dose, in particular 1 to 25 mg per individual dose are suitable for administration to larger mammals, in particular humans.

As therapeutic agents, the compounds of Formula I may be contained with customary pharmaceutical auxiliaries in pharmaceutical preparations such as e.g. tablets, capsules, suppositories or solutions. These galenic formulations can be prepared by known methods using conventional solid or liquid excipients, e.g. lactose, starch or talcum or liquid paraffins, and/or using conventional pharmaceutical auxiliary substances, for example tablet disintegrants, solubilizers or preservatives.

The following examples are intended to illustrate the invention in further detail without limiting its scope.

EXAMPLE 1

7-(n-Butyl)-3-(2,4-dinitrophenyl)-9,9-dimethyl-3,7-diazabicyclo[3.3.1]nonane

A solution of 4.7 g 7-(n-butyl)-9,9-dimethyl-3,7-diazabicyclo [3.3.1]nonane in 10 ml acetone was added dropwise to a solution of 4.2 g 2,4-dinitrofluorobenzene in 40 ml acetone with stirring. Stirring of the reaction mixture was continued at room temperature and the mixture was left to stand overnight. Then acetone was withdrawn and aqueous citric acid solution was added to the residue and this mixture was extracted twice with ethyl acetate. For further working-up, the aqueous residue was rendered alkaline with dilute sodium hydroxide solution. This mixture was again extracted twice with ethyl acetate. The combined organic phases were dried with magnesium sulfate and reduced. The residue was recrystallised from ether/hexane. 5.5 g 7-(n-butyl)-3-(2,4-dinitrophenyl)-9,9-dimethyl-3,7-diazabicyclo-[3.3.1]nonane with a melting point of 119° C. were obtained.

0.61 g of the title compound was dissolved in 10 ml isopropanol with heating in an oil bath. 0.7 ml of a 3.8 n isopropanolic hydrochloric acid solution was added to the solution. Then the reaction mixture was allowed to cool and the resulting crystals were filtered out. 0.5 g of the hydrochloride of the title compound with a melting point of 136–138° C. were obtained.

The compounds of Formula I set forth in the following Table F can also be prepared according to the processes described in the above example or to processes analgous thereto.

TABLE F

| Ex. No. | $R^1$ | $R^2$ | $R^3$ | $R^4$ | Salt | Mp. in ° C. |
|---|---|---|---|---|---|---|
| 2 | n-$C_4H_9$— | $CH_3$— | $CH_3$— | 4-$NO_2$—phen | B | 116–118 |
| 3 | n-$C_4H_9$— | —$(CH_2)_4$— | | 4-$CH_3$CO—phen | 1 HTa | 111 |
| 4 | n-$C_4H_9$— | —$(CH_2)_4$— | | 4-CN—phen | 1 HTa | 115 |
| 5 | n-$C_4H_9$— | n-$C_3H_7$— | $CH_3$— | 4-CN—phen | 1 HTa | am |
| 6 | n-$C_6H_{13}$— | $CH_3$— | $CH_3$— | 4-CN—phen | 1 HTa | am |
| 7 | Cyp-$CH_2$— | —$(CH_2)_4$— | | 4-CN—phen | B | 101–103 |
| 8 | i-$C_4H_9$— | —$(CH_2)_5$— | | 4-CN—phen | 1 HCl | 138–142 |
| 9 | $CH_3$— | —$(CH2)_5$— | | 4-CN—phen | 1 HCl | 270 |

Cyp = cyclopropyl, n = normal, i = iso, HTa = hydrogen tartrate, HCl = hydrochloride, B = base, am = amorphous

EXAMPLE I

Tablets Containing 7-(n-Butyl)-3-(4-cyanophenyl)-9,9-tetramethylene-3,7-diazabicyclo[3.3.1]nonane Hydrogen Tartrate Tablets were prepared having the following composition per tablet:

| | |
|---|---|
| 7-(n-butyl)-3-(4-cyanophenyl)-9,9-tetramethylene-3,7-diazabicyclo-[3.3.1]nonane hydrogen tartrate | 20 mg |
| Corn starch | 60 mg |
| Lactose | 135 mg |
| Gelatine (as 10% solution) | 6 mg |

The active substance, the corn starch and the lactose were thickened using the 10% strength gelatine solution. The paste was comminuted, and the resulting granules were transferred to a suitable tray and dried at 45° C. The dried granules were passed through a crusher and mixed in a mixer with the following further auxiliaries:

| | |
|---|---|
| Talcum | 5 mg |
| Magnesium stearate | 5 mg |
| Corn starch | 9 mg | and then compressed to give 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I:

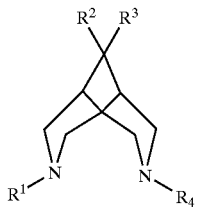

I wherein $R^1$ is an alkyl group with 1–6 carbon atoms or a cycloalkylalkyl group with 4–7 carbon atoms, $R^2$ is lower alkyl, and $R^3$ is lower alkyl, or $R^2$ and $R^3$ together form an alkylene chain with 3–6 carbon atoms, and $R^4$ represents a phenyl radical monosubstituted in the ortho or para position by nitro, cyano or lower alkanoyl or disubstituted in the ortho and para positions by nitro;

or a physiologically compatible acid addition salt thereof.

2. A compounds according to claim 1, wherein $R^4$ is a phenyl radical monosubstituted in the para position by cyano or lower alkanoyl.

3. A compounds according to claim 1, wherein $R^1$ is an alkyl group with 3–5 carbon atoms, and $R^2$ and $R^3$ together form an alkylene chain with 3 to 6 carbon atoms.

4. 7-(n-butyl)-3-(4-cyanophenyl)-9,9-tetramethylene-3,7-diazabicyclo[3.3.1]nonane according to claim 1.

5. 7-(n-butyl)-3-(4-acetylphenyl)-9,9-tetramethylene-3,7-diazabicyclo[3.3.1]nonane according to claim 1.

6. A pharmaceutical composition comprising a pharmacologically active amount of a compound according to claim 1 and at least one pharmaceutical auxiliaries or carrier.

7. A method of inhibiting cardiac arrhythmia in a mammal comprising administering to said mammal an effective cardiac arrhythmia inhibiting amount of a compound according to claim 1.

8. A process for preparing a compound corresponding to formula I

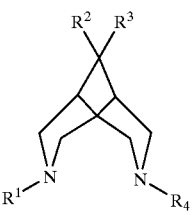

I wherein $R^1$ is an alkyl group with 1–6 carbon atoms or a cycloalkylalkyl group with 4–7 carbon atoms, $R^2$ is lower alkyl, and $R^3$ is lower alkyl, or $R^2$ and $R^3$ together form an alkylene chain with 3–6 carbon atoms, and $R^4$ represents a phenyl radical monosubstituted in the ortho or para position by nitro, cyano or lower alkanoyl or disubstituted in the ortho and para positions by nitro, or a physiologically compatible acid addition salt thereof, said method comprising reacting a compound corresponding to formula II

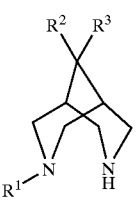

II wherein $R^1$, $R^2$ and $R^3$ have the above meanings, with a compound corresponding to formula III $R^4$–X   III wherein $R^4$ has the above meaning and X is halogen, and optionally converting a free base of Formula I into a corresponding acid addition salt or converting an acid addition salt of a compound corresponding to formula I into the corresponding free base.

* * * * *